(12) United States Patent
Hortenstine

(10) Patent No.: US 8,684,907 B2
(45) Date of Patent: Apr. 1, 2014

(54) ADJUSTABLE INCONTINENCE APPARATUS

(76) Inventor: Jay S. Hortenstine, Murrayville, GA (US)

( * ) Notice: Subject to any disclaimer, the term of this patent is extended or adjusted under 35 U.S.C. 154(b) by 617 days.

(21) Appl. No.: 12/036,345

(22) Filed: Feb. 25, 2008

(65) Prior Publication Data

US 2008/0269547 A1 Oct. 30, 2008

Related U.S. Application Data

(60) Provisional application No. 60/891,554, filed on Feb. 26, 2007.

(51) Int. Cl.
*A61F 2/02* (2006.01)

(52) U.S. Cl.
USPC ............................................................ 600/30

(58) Field of Classification Search
USPC ......... 600/29–32, 37; 128/885; 606/228, 151; 623/23.66, 23.67
See application file for complete search history.

(56) References Cited

U.S. PATENT DOCUMENTS

| | | | |
|---|---|---|---|
| 6,117,067 A | 9/2000 | Gil-Vernet | |
| 6,612,977 B2 | 9/2003 | Staskin | |
| 6,638,211 B2 | 10/2003 | Suslian | |
| 6,911,003 B2 | 6/2005 | Anderson | |
| 7,083,637 B1 | 8/2006 | Tannhauser | |
| 7,244,259 B2 | 7/2007 | Smith | |
| 7,395,822 B1* | 7/2008 | Burton et al. | 128/885 |
| 2002/0156487 A1* | 10/2002 | Gellman et al. | 606/139 |
| 2003/0216814 A1 | 11/2003 | Siegel | |
| 2004/0215054 A1 | 10/2004 | Siegel | |
| 2004/0249240 A1 | 12/2004 | Goldmann | |
| 2005/0027160 A1 | 2/2005 | Siegel | |
| 2005/0055104 A1 | 3/2005 | Arnal | |
| 2006/0058574 A1* | 3/2006 | Priewe et al. | 600/29 |
| 2007/0049790 A1* | 3/2007 | Wagner et al. | 600/37 |

* cited by examiner

*Primary Examiner* — Christine Matthews
(74) *Attorney, Agent, or Firm* — Joseph M. Lewinski; Lynda F. Kouroupis

(57) ABSTRACT

In an exemplary embodiment an adjustable urethral sling includes a flexible mesh support having a mesh envelope at a suburethral potion and an expansion chamber within the mesh envelope. A conduit may be provided that extends along the flexible mesh support and that is in fluid communication with the expansion chamber. When installed in a patient the sling may loop under the urethra and out exit sites. An access port may be provided in a subcutaneous pocket and attached to the conduit to allow for remote expansion of the expansion chamber from a desirable location to allow adjustment of the sling with the patient in a standing position. The mesh envelope allows tissue ingrowth around the container so that the container can be expanded for a long period of time after implantation. The expansion chamber may be U-shaped to provide lateral closing pressure to the urethra when expanded.

23 Claims, 12 Drawing Sheets

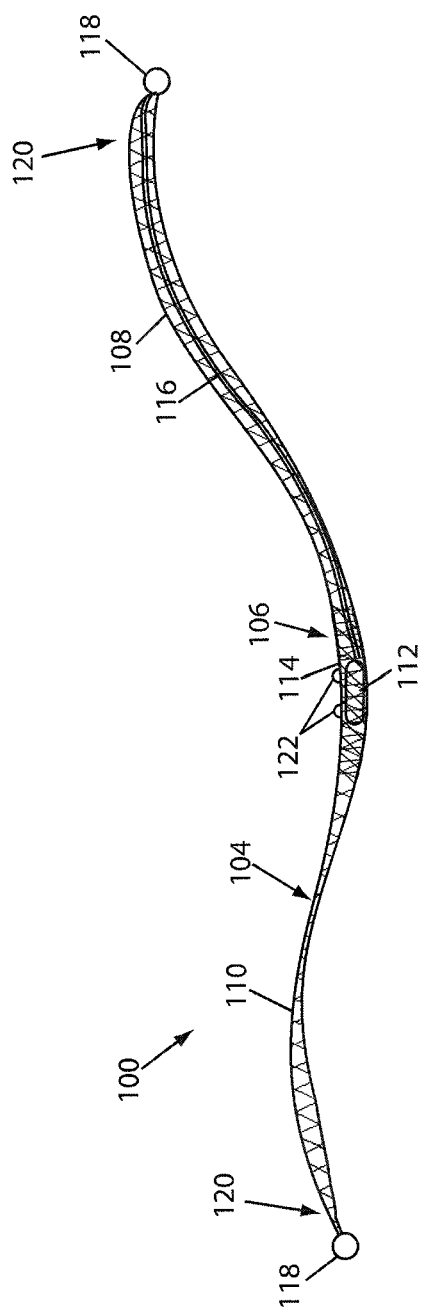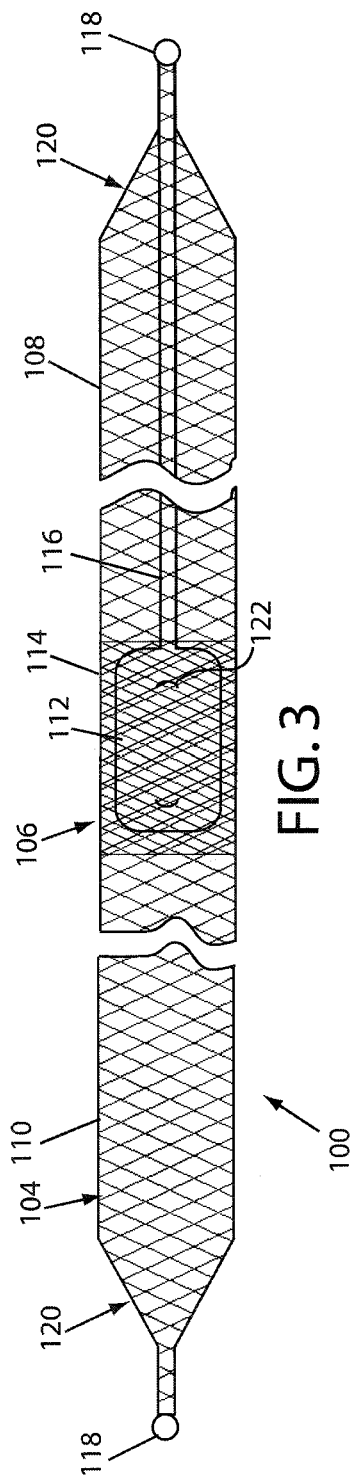

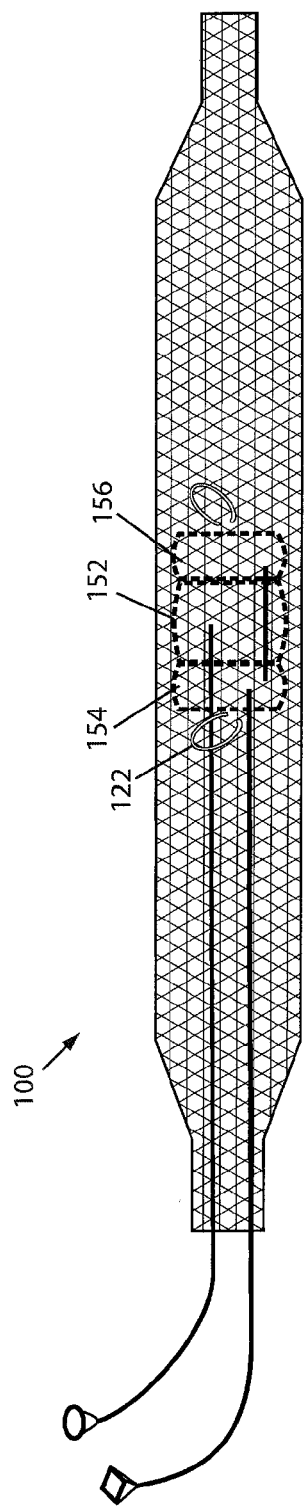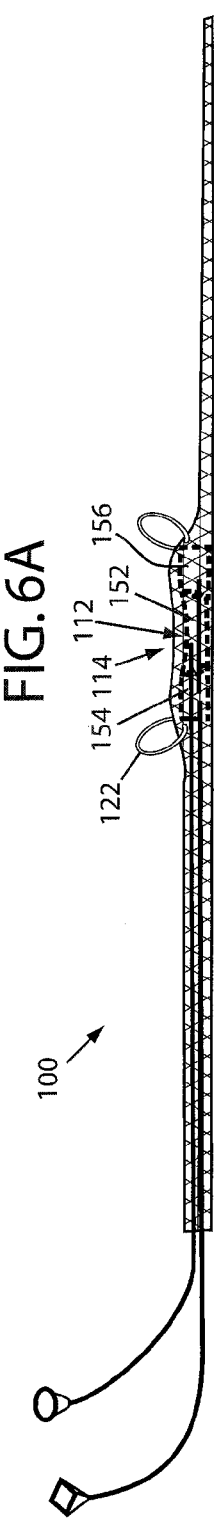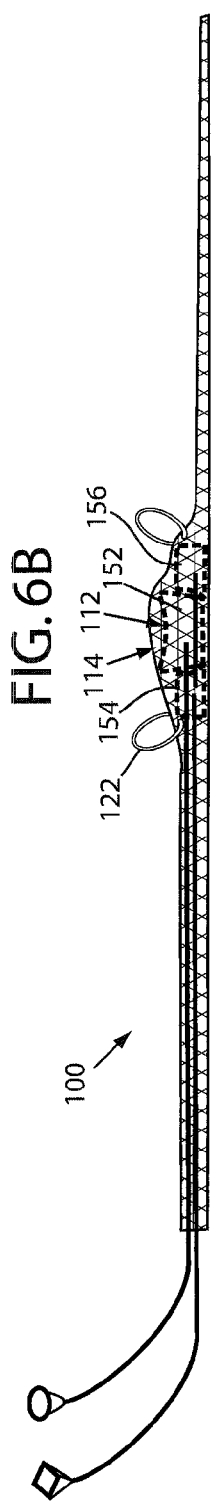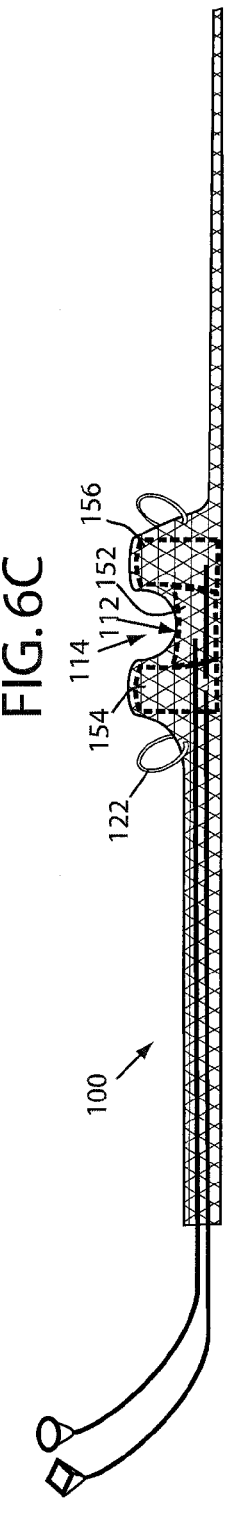

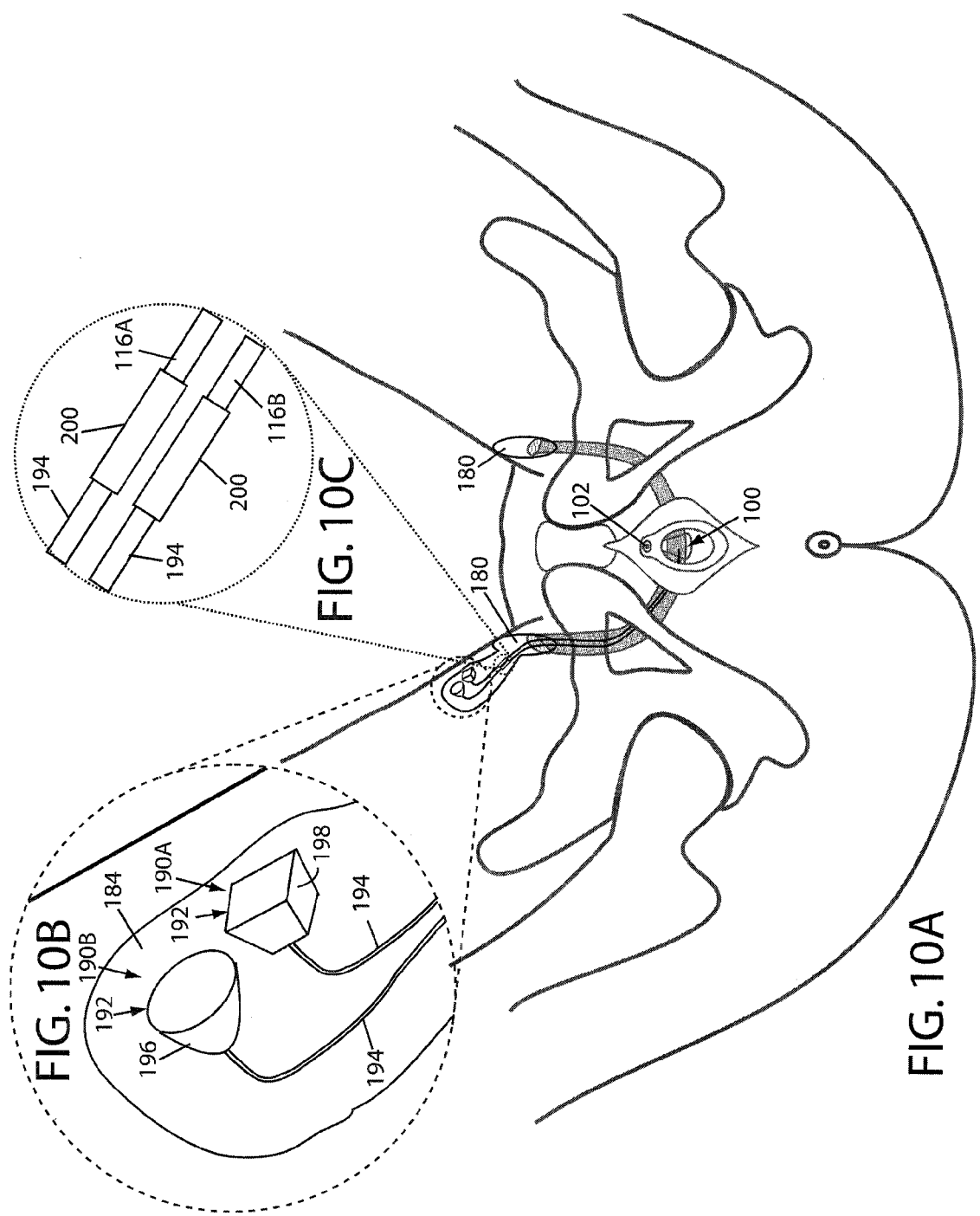

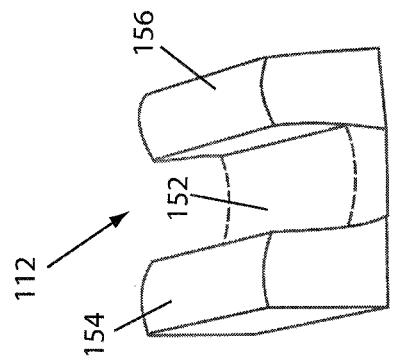
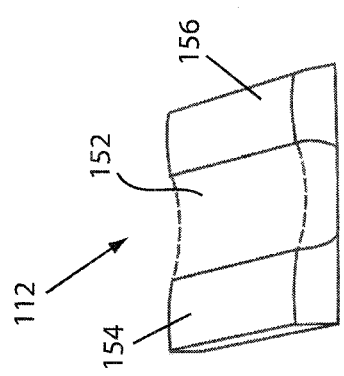
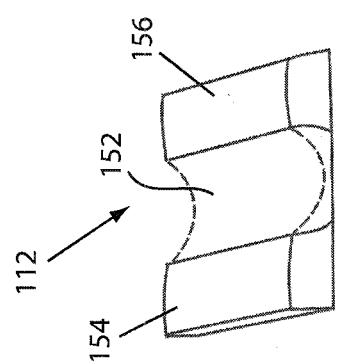

ADJUSTABLE INCONTINENCE APPARATUS

CROSS-REFERENCE TO RELATED APPLICATIONS

This application claims priority to co-pending U.S. Provisional Application No. 60/891,554 filed Feb. 26, 2007, which is entirely incorporated herein by reference.

FIELD OF THE INVENTION

The present invention relates to apparatus and methods for treating urinary incontinence, and more particularly, to urethral slings for treating stress urinary incontinence.

BACKGROUND

The unintentional leakage of urine, known as urinary incontinence, afflicts about 13 million people in the United States. One type of urinary incontinence, referred to as stress urinary incontinence (SUI), is the unintentional urine leakage during times of abdominal stress, such as that which may occur during coughing, laughing, or sneezing. One cause of SUI is inadequate anatomical support of the urethra which allows the urethra to move out of the retropubic space and rotate into the vagina. This condition is known as "hypermobility of the urethra" or simply "hypermobility." SUI may also result from insufficient closing pressure of the urethra which prevents the urethra from fully collapsing and sealing. This condition is known as intrinsic sphincter deficiency (ISD).

SUI patients are generally categorized into three types: Type I, Type II, and Type III, depending upon a patient's particular symptoms. A Type I SUI patient is classified as a patient that has involuntary urine leakage without hypermobility. Type I SUI is the mildest and least common type of UI, being present in only about 13% of SUI patients.

Type II SUI refers to patients with urethral hypermobility. Type II is the most common type of SUI, afflicting about 37% of SUI patients. Type II SUI is most commonly found in women and is often a result of child birth which can weaken the anatomical structure that supports the urethra.

Type III SUI refers to patients with ISD. Type III SUI is the second most common type of SUI and is estimated as being the solitary cause of incontinence in about 33% of SUI patients. As mentioned above, unlike Type II SUI, which is due to a lack of anatomical support and associated hypermobility, Type III SUI is a result of a defect in the urethra itself, in which the urethra fails to fully close. Type III SUI is often caused by scarring of the urethra which prevents the urethra from properly collapsing and sealing. It has recently been suggested however, that every woman with stress incontinence has some component of Type III (ISD).

A variety of devices have been developed for the treatment of SUI. For example, urethral slings are commonly used to treat the hypermobility associated with Type II SUI and artificial sphincters have been used to treat ISD. To treat SUI, a urethral sling is typically implanted below the urethra to provide support under the urethra and prevent unwanted movement of the urethra down into the vagina. A variety of different slings and associated implantation methods have been developed. Early pubovaginal slings were designed for placement toward the posterior urethra at its junction with the bladder neck to raise the urethra and/or bladder neck from a descended position.

More recent slings have been implanted at midurethra under no tension. These midurethral slings are generally not intended to raise the urethra but to provide a "backboard" for the urethra to prevent the unwanted urethral movement associated with hypermobility. A typical midurethral sling comprises a tape that is implanted using a transvaginal approach in which opposite ends of the tape are arranged on opposite sides of the urethra so that the tape loops under the urethra to form a sling. The tape is typically implanted using needles that attach to the tape of the sling so that the tape's ends can be inserted into the body and exit out of the body at a desired exit site. Excess tape extending out of the body can be removed and the remainder of the tape left in the body to act as a sling. The sling is held in place by friction.

More specifically, a tension-free vaginal tape (TVT) has been developed that may be implanted using a transvaginal approach in which the tape is implanted below the urethra and exits the abdominal wall. Another device, known as transobturator tape (TOT), has been developed and a method for implanting TOT developed by Delome, in which the TOT is placed between two obturator foramen to create a hammock to support the urethra. The TOT may be inserted around the ischiopubic ramus in a horizontal plane through the two obturator foramina. More recently, TVT-O tape has been developed for implantation using a method of penetrating the obturator foramen from the vaginal incision towards the thigh fold.

These urethra slings have proven successful in treating up to 90% of Type II patients, but have a long term effectiveness of only about 74% in Type III (ISD) or mixed Type II and Type III cases. The failure of these slings may be due to dislocation of the sling. For example the sling may become dislocated from its desired midurethral position and move back toward the bladder. In addition, even if a sling is properly positioned, thereby curing the hypermobility, the patient may also suffer from ISD which the sling may not adequately address.

Presently, there are few good alternatives for assisting those patients for whom a urethral sling fails to provide a satisfactory continence level. One option is to install an additional urethral sling. But adding an additional sling results in a complicated support system that entails another invasive surgery.

Another approach is to try to provide additional closing pressure to the urethra to treat possible ISD. As previously mentioned, artificial sphincters have been used to increase urethral closing pressure. In addition to requiring invasive surgery, these devices tend to be large and complicated and designed to treat patients with a high level of ISD. Many patients are resistant to having two surgeries and two incontinence devices. It would be desirable to have a single device that could address both hypermobility and ISD and be implanted in a single surgery.

Another technique to increase closing pressure of the urethra is to inject a bulking agent into the tissue surrounding the urethra to increase support about the urethra. While this technique has shown to be useful in improving continence levels of patients, its effect is only temporary due to the absorption of the bulking agent by the body over time. Accordingly, a patient will often require repeated injections in order to maintain a desired level of continence. In addition, the injection of the bulking agent directly into the tissue is not easily undone once injected and can lead to severe complications in the event too much bulking agent is injected. Side effects can be especially serious when more permanent bulking materials are used. Direct tissue injections also do not provide a structure for tissue ingrowth about the injection site and therefore often result in encapsulation and the development of scar tissue. The injections may also lead to fluid collections around the injections which can lead to infection. Further, once injected, the bulking agent is not easily removed. This may lead to serious complications if too much bulking agent is injected which compresses the urethra to the point that the patient is unable to urinate. In those cases, the patient must then rely on self-catheterization to empty the bladder. The injections may also raise the urethra to an undesired height.

Another option is to adjust the implanted sling itself. For example, many surgeons attempt to improve continence by pulling on the ends of the sling to increase the sling tension. This seldom has a positive effect and often results in further complications such as de novo urge incontinence. For example, tightening the sling tends to raise the urethra as the sling is pulled taught which can move the urethra to a position higher than desired. In addition, attempting to tighten the sling often dislocates the sling from its desired mid-urethra location to a position back toward the bladder. This can lead to "urge" incontinence in which a patient has symptoms of overactive bladder, thereby leaving the patient worse off after surgery than before. In addition, tightening the sling does not provide a uniform closing pressure about the bottom and sides of the urethra as most of the force will be concentrated at the bottom of the urethra when the sling is pulled tight. In order to apply sufficient closing pressure to the urethra the sling must therefore be pulled very tight so that the upward force to the bottom of the urethra is sufficient to force the urethra to close, effectively strangling/occluding the urethra. Furthermore, as discussed above, for best performance the sling should not be under tension.

A few slings have been developed that provide for postoperative adjustment of some type, but the adjustment of such slings is typically complicated, difficult, and invasive. These slings also tend to be susceptible to dislocation from a desired midurethral position during adjustment. The prior art slings also tend to be promote scar tissue development. Therefore, the prior art adjustable slings typically require adjustment soon after surgery before scar tissue develops and prevents the fine tuning of the sling. These slings are also prone to raising the urethra to an undesired height during adjustment.

U.S. Pat. No. 6,117,067 to Gil-Vernet teaches the implantation of a urethral sling beneath the urethra that is adjustable to raise the urethra. The sling is connected by threads to an expandable container implanted remotely from the urethra, such as in the adipose tissue. The sling may be tightened by injecting bulking agent into the remote container to lift the strings and thereby lift the sling and raise the urethra. While fit for its intended purpose, that procedure is complicated, requiring insertion of both the sling and the container in different sites. Furthermore, as discussed above, tightening the tension of the sling tends to raise the urethra to an undesired height. Furthermore, tightening the sling does not provide uniform pressure about the bottom and sides of the urethra or provide means to accurately manage such bottom and side forces, as most of the force will be applied beneath the urethra. Furthermore, studies have shown that it is desirable to leave the sling non-tensioned for correcting hypermobility.

U.S. Pat. No. 7,083,637 to Tannhauser discloses a urethral sling, referred to as a tape, that may be adjusted post-operatively to change support under the urethra. Tannhauser teaches implanting a sling using a retropubic approach in which curved needles are used to pass one end of the tape into the body via the vagina at one side of the urethra and over the pubis and through the abdominal wall and pass a second end of the tape on the other side of the urethra in the same manner to form a sling around the urethra. Mechanical adjusting means may be provided in the form of sutures located on the tape to adjust the length of one or both sides of the tape in near proximity to the urethra to adjust the effective length of the supporting arms of the tape. The sutures remain accessible through the incision in the vagina for a period of time after implantation, such as a few days to adjust the length of the supporting arms of the tape used to support the urethra.

Tannhauser also teaches attaching an expandable container to the tape and implanting the tape so that the container is between the tape and the urethra. The sling may be adjusted postoperatively by injecting bulking agent directly into the expandable container or to a port located in close proximity to the container. To inject the bulking agent the surgeon must make an injection into the vagina. Not only can this be uncomfortable for the patient but it is difficult to accomplish and raises the possibility of inadvertently puncturing the bladder or urethra. According to Tannhauser, upon injection of bulking agent into the expandable container, the tissue between the mesh and the urethra will expand resulting in a simple vertical lifting due to expansion and a vertical lifting due to stretching the outside of the mesh.

While fit for its intended purpose, Tannhauser has several drawbacks. First, the location of the expandable container and injection port within the vagina make it difficult to locate and inject the bulking agent, likely requiring a vaginal incision to re-expose the container or injection port. The difficulty in locating the expandable chamber or injection port make injecting the bulking agent into the container a complicated and risky process that will require repeated vaginal incisions and vaginal needle punctures to inject the bulking agent. The positioning of the injection port in the vagina will likely be poorly received by a sexually active patient and may lead to dyspareunia.

Tannhauser also does not provide for normal tissue ingrowth between the urethra and the container resulting in the development of scar tissue. Tannhauser teaches attaching the expandable container to the tape so that the chamber is exposed to the tissue between the urethra and the tape. This arrangement will promote the development of scar tissue, which lacks the resilience of ingrowth tissue, and once the capsule of scar tissue has developed around the container, it will prevent expansion of the container. The Tannhauser device must therefore be adjusted within a few days after surgery before the development of scar tissue which would prevent the expansion of the container. Scar tissue will also prevent adjustment of the container to provide additional support as the patient ages. Adjustment of the Tannhauser device also requires that the patient be in a lithotomic or supine position. However, testing patient incontinence requires the patient to stand. Thus, the patient will be forced to alternate between the standing and supine position during the adjustment process.

Expansion of the Tannhauser arrangement will also apply most of the force to the bottom of the urethra and without providing significant lateral support. Nor will the device provide lateral support that is adjustable independently of the lower support to provide a more uniform closing pressure. Thus, in order to provide sufficient urethral closing pressure, the container of Tannhauser would need to be inflated to a large size in order to provide sufficiently large force to the bottom of the urethra. This is likely to cause dislocation of the sling from the desired mid-urethral location to a position near the bladder which can lead to urge incontinence. In addition, the expansion of the container may position the urethra to a position higher than desired or significantly increase the tension on the sling. Furthermore, Tannhauser will not provide effective treatment for male incontinence, as the device would likely slide posteriorly off of the bulbous urethra and allow pressure to be applied directly to the anterior rectal wall, providing no beneficiary urethral compression or relocation.

What is needed is a urethral sling that effectively addresses both hypermobility and ISD. What is also needed is an incontinence device that is postsurgically adjustable to a patient's needs. What is also needed is a tension free urethral sling that can be adjusted to provide increased urethra pressure without causing dislocation of the sling. What is also needed is a tension free urethral sling that can be adjusted to increase urethral closing pressure without significantly increasing the tension on the sling. What is also needed is a urethral sling that is easily adjustable after surgery to provide increased support to the urethra without significantly changing the position (height) of the urethra. What is also needed is a urethral sling that promotes tissue ingrowth and minimizes infection risks. What is also needed is a urethral sling that is adjustable over long periods such as years. What is needed is a urethral sling that is easily adjustable after surgery without incisions or invasive surgery. What is needed is a sling that can be adjusted while the patient is in the standing position. What is also needed is a device that does not interfere with the sex life of the patient. What is also needed is a device that is suited to treat both male and female incontinence.

SUMMARY OF THE INVENTION

In one exemplary embodiment, a urethral sling comprises a flexible mesh support, an expansion chamber, and a mesh envelope for housing the expansion chamber. The flexible mesh support is adapted for implantation into the body and may include a suburethral portion for placement under the urethra and trimmable end portions for extending out of exit sites when the sling is implanted in a patient's body. The expansion chamber may be provided at the suburethral portion and adapted to expand within the mesh envelope to a desired shape to supply a desired closing pressure to the urethra for the treatment of ISD.

The mesh envelope may be a collapsible mesh structure for housing the expansion chamber to promote tissue ingrowth around the expansion chamber. A trimmable conduit may be provided that is in fluid communication with the expansion chamber and extend along to the flexible mesh support. The conduit provides means for remote injection of an expansion fluid into the expansion chamber from a remote access port. The conduit may comprise a small diameter non-kink tube fluidly coupled to a subcutaneous access port by a connector so that fluid injected into the access port passes through the conduit into the expansion chamber to expand the chamber and provide closing pressure to the urethra. In an exemplary embodiment, the access port comprises an injection port with a flow tube that may be placed in a subcutaneous pouch and fluidly connected to the conduit using a connector. In an exemplary embodiment, the access port may be similar to a port-a-cath and the flow tube connected to the conduit using a quick connect connector. In an embodiment which employs more than one conduit, multiple access ports may be used. In one exemplary embodiment access ports have palpably different shapes to allow a physician to readily identify a desired access port and determine which access port is associated with which expansion chamber or chambers. For example, a round-walled injection port may be coupled to a first subchamber and a square-walled injection port may be coupled to a second and third subchamber. This allows for easy adjustment of the sling and tight control over the urethral closing pressure applied by the sling.

The expansion chamber may be in an initial collapsed position within the mesh envelope to allow for easy implantation into the body. The expansion chamber may be sized and shaped so as to expand in a predetermined manner when filled with an expansion fluid. In an exemplary embodiment, the expansion chamber has a general U-shape with a lower center portion for positioning under the urethra and providing an upward closing pressure to the urethra when expanded, and left and right outer portions for providing lateral support and lateral closing force to the urethra when expanded. This allows the expansion chamber to form a U-shaped cradle that provides both lower and lateral closing pressure to the urethra.

The expansion chamber may comprise portions with differing expandability to further control the expansion of the expansion chamber. For example, a bottom portion of the expansion chamber may be of a first material that resists expansion and an upper portion of the expansion chamber may be of a material of greater expandability so that when fluid is provided to the expansion chamber the upper portion expands and the lower portion does not.

In one exemplary embodiment, the expansion chamber may comprise a single chamber and in other embodiments may comprise multiple subchambers. For example, a U-shaped expansion chamber may comprise a center subchamber between two outer lateral subchambers. The conduit may be coupled to one or more expansion chambers. In addition, multiple conduits may be used that are associated with particular expansion chambers or subchambers.

The mesh envelope houses the expansion chamber and provides a scaffold for tissue ingrowth about the expansion chamber so that scar tissue does not form an unwanted capsule around the expansion chamber. The mesh envelope may be of different shapes and sizes to allow for a desired expansion of the expansion chamber to provide a desired closing force to the urethra when expanded. For example, the mesh envelope may be in the shape of a collapsed U with a center portion of a first height that is associated with the center portion of a U-shaped expansion chamber to allow for the expansion of the center portion to a desired size below the urethra, and opposite outer portions of a greater extendable height that is associated with the outer portions of the U-shaped expansion chamber to allow for expansion of the outer portions of the expansion chamber at the left and right of the urethra.

Attachment means may be provided for attaching the mesh envelope to periurethral tissue about the urethra. This helps prevent dislocation of the sling when the sling is adjusted by expanding the expansion chamber. In one embodiment, one or more eyelets may be provided on the mesh envelope to allow a surgeon to place a suture through the eyelet and periurethral tissue. This allows the mesh envelope to be attached about the urethra at a desired position to serve as a guide for directing the expansion of the expansion chamber. For example, outer portions of the collapsed mesh envelope which will house the outer portions of a U-shaped expansion chamber may be attached to the periurethral tissue adjacent to the left and right lateral sides of the urethra so that the mesh envelope extends from the left side of the urethra, below the urethra to the right side of the urethra. This provides an expansion guide for the expansion chamber to provide lateral closing pressure to the urethra.

In an exemplary embodiment of a system of the invention, an access port may be provided at a remote site from the urethra that is fluidly connected to the conduit to allow for the addition or removal of fluid into and from the expansion chamber. A connector, such as a snap connector, may be provided at the ends of the mesh support to attach to a trocar or other surgical implement to implant the sling in the patient's body. The conduit may extend from the expansion chamber along the mesh support so that when the mesh support is implanted into the body and out the exit sites, the conduit follows the same path.

In one exemplary embodiment, the mesh support is in the form of a mesh tape having outer portions comprising a single mesh layer, and a mesh envelope comprising a double mesh layer. In that embodiment, the conduit may be attached to the mesh support with an adhesive so that the conduit follows the path of the mesh support. In another exemplary embodiment, the mesh support is in the form of a mesh tube and the mesh envelope is an enclosed section of the tube. In that embodiment, the conduit may extend along the mesh support within the interior of the mesh tube.

The mesh support is implanted into the patient's body so that the suburethral portion of the sling loops below the urethra and the ends of the mesh support extend out of the body at exit sites. In an exemplary method a transobturator approach may be used so that the sling extends between the obturator foramina with no tension and exits out of the body near the inner thigh. Other approaches may be used however, with other exit sites, such as, by way of example and not limitation, a retropubic approach with exit sites near the abdomen. An excess portion of the mesh support and conduit may be trimmed and the remainder of the mesh support and conduit left in the body. A subcutaneous pocket may be made extending from the exit site to a desired access area. An access port having associated tubing may be inserted into the subcutaneous pocket and fluidly coupled to the conduit. A connector may be used to connect the conduit and injection port to provide fluid communication between the injection port, the conduit and the expansion chamber. To adjust the closing pressure on the urethra a physician can simply add or remove expansion fluid from the expansion chamber by adding or removing fluid from the injection port using a syringe.

By housing the expansion chamber within the mesh, the development of scar tissue will be minimized while allowing tissue ingrowth in the mesh. This provides resilient tissue around the expansion chamber to allow the expansion chamber to be expanded, days, months, or even years after implantation. By providing attachment means for attaching the mesh envelope to the periurethral tissue and providing a guide for the expansion chamber to expand, a desired U-shaped cradle can be generated that provides lateral urethral closing pressure without dislocating the sling or raising the urethra to an undesirable height. By providing a conduit that is fluidly coupled to the expansion chamber that extends along the mesh support, a desirable remote access location can be readily provided that can be easily located and accessed when the patient is in a standing position.

The device can be installed in a single surgery with local anesthesia. If the patient has good results after the installation of the apparatus, then a physician need not adjust the apparatus to provide additional support. If, on the other hand, the patient has not achieved a desired level of continence, then the physician can adjust the amount of closing pressure provided to the urethra by simply injecting an expansion fluid into the access port(s) to expand the expansion chamber(s). Expansion fluid can also be removed from the chamber as needed. The access port may be located remotely from the expansion chamber at a desirable location for both the patient and the physician, such as at the inner thigh. This allows for easy access to the access port while the patient is standing thereby allowing the sling to be adjusted and tested in the standing position, which is the position most commonly associated with SUI in women.

BRIEF DESCRIPTION OF THE DRAWINGS

FIG. 2 shows an exemplary embodiment of an adjustable urethra sling.

FIG. 3 shows a top plan view of an exemplary embodiment of an adjustable urethra sling.

FIGS. 6A-6D show different shapes of an expanded urethral sling in accordance with an exemplary embodiment of the invention.

FIG. 10A shows a urethral sling system implanted in a patient with an access port located at the inner thigh in accordance with an exemplary embodiment of the invention.

FIG. 10B shows an enlarged view of portion B-B of FIG. 10A.

FIG. 10C shows an enlarged view of portion C-C of FIG. 10A.

FIGS. 11A-11C show an exemplary embodiment of an expansion chamber that is expanded into different shapes.

DESCRIPTION

As required, exemplary embodiments of the present invention are disclosed herein. These embodiments are meant to be examples of various ways of implementing the invention and it will be understood that the invention may be embodied in alternative forms. The figures are not to scale and some features may be exaggerated or minimized to show details of particular elements, while related elements may have been eliminated to prevent obscuring novel aspects. Therefore, specific structural and functional details disclosed herein are not to be interpreted as limiting, but merely as a basis for the claims and as a representative basis for teaching one skilled in the art to variously employ the present invention. While in the exemplary embodiments the apparatus is discussed in the context of female incontinence, the device may be used in males as well.

Figure 1:
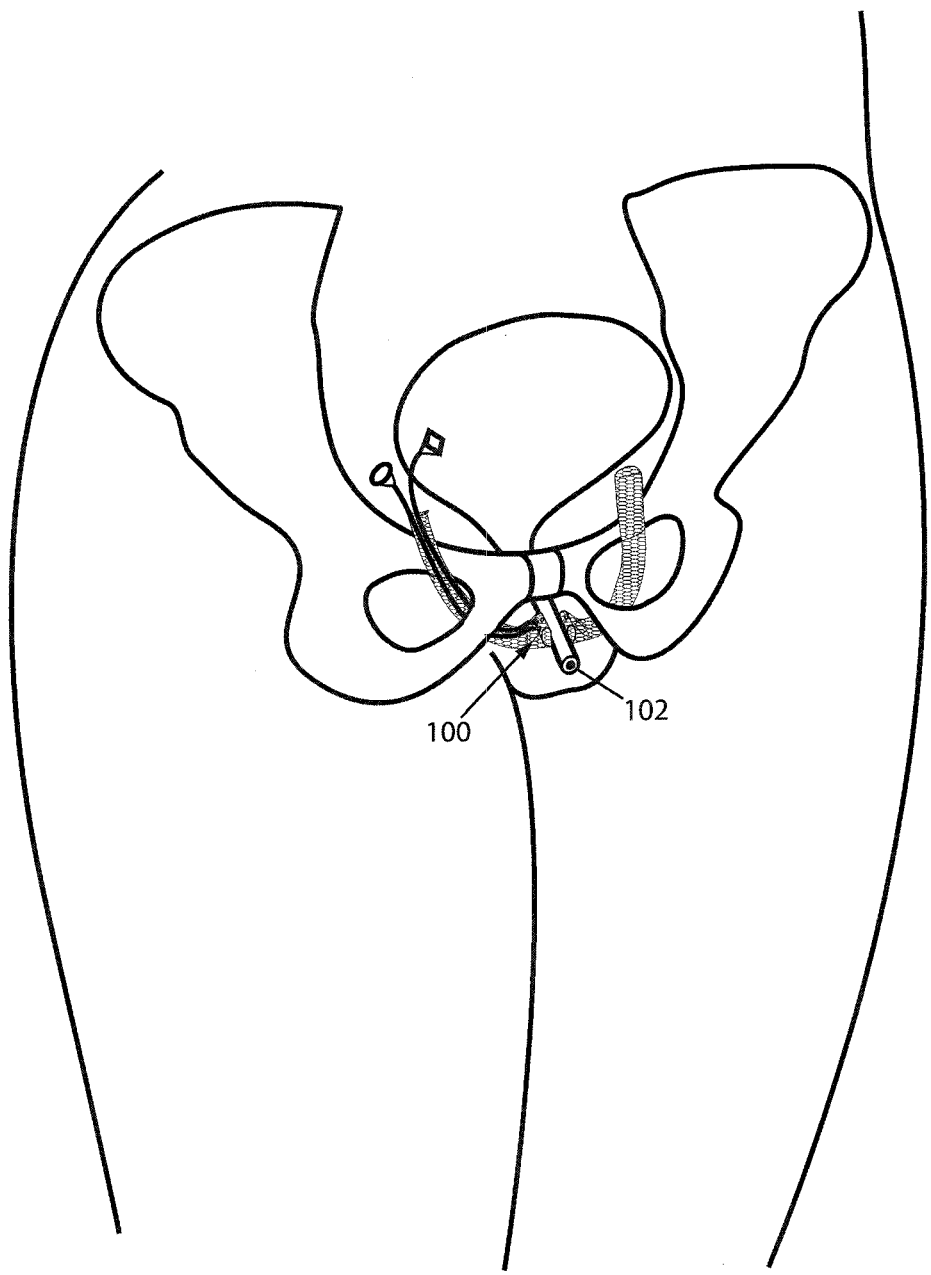
FIG. 1 shows an exemplary embodiment of an adjustable urethra sling installed in a patient.

Turning to the figures wherein like reference numbers represent like features, FIG. 1 shows an exemplary embodiment of an adjustable urethral sling 100 implanted in a patient for the treatment of stress urinary incontinence by providing support and closing pressure to a urethra 102. FIGS. 2 and 3 show the sling 100 in an initial collapsed condition prior to implantation into a patient's body.

As shown in FIG. 2, the sling 100 may include an elongated support or tape, such as a flexible mesh support 104, adapted for implantation into the body. The mesh support 104 may include a center suburethral portion 106 between two outer portions 108, 110. The suburethral portion 106 may be adapted for placement under the urethra of a patient and the outer portions 108, 110 adapted for extending out of the body at predetermined exit sites during implantation in the patient so that the sling 100 loops under the urethra. An expansion chamber 112 may be provided at the suburethral portion 106 which may be expanded by the addition of expansion fluid to apply a desired closing pressure to the urethra. The expansion chamber 112 may be housed within a mesh envelope 114 which promotes tissue ingrowth around the expansion chamber 112 after implantation of the sling 100 in a patient. In an exemplary embodiment, shown in FIG. 2 an expansion chamber 112 may be in the form of a 1 cm×1.5 cm flat silicone inflatable balloon.

The sling 100 may be of an initial length for implantation that may be adjusted to a desired size by removing an excess portion after implantation into the patient. In an exemplary embodiment shown in FIG. 2, the outer portions 108, 110 may be formed of a single layer mesh and the mesh envelope 114 formed of a double layer mesh that provides a mesh enclosure for enclosing the expansion chamber 112. In another exemplary embodiment the mesh support 104 may be in the form of a mesh tube. The sling 100 may be housed within a removal sheath (not shown) to ease movement of the sling through the body during implantation.

A conduit 116 may be provided that is in fluid communication with the expansion chamber 112. As described later, after implantation, the conduit may be fluidly coupled to a fluid source. The conduit 116 may comprise a small diameter, kink-resistant tubing adapted to provide a path for the flow of expansion fluid into the expansion chamber 112. The conduit 116 thereby provides means for adjusting the sling 100 from a remote location. For example, the conduit 116 may coupled to an access port in which a syringe may be inserted to inject or remove expansion fluid to or from the expansion chamber 112 and thereby expand or contract the expansion chamber 112 to increase or decrease the closing forces applied to the urethra. As shown in FIGS. 2 and 3, the conduit 116 may be attached to, and follow the course of, the outer portion 108 of the mesh support 104. For example, the conduit 116 may be adhered to the surface of the outer portion 108 by an adhesive in embodiments in which the outer portion 108 is a single layer mesh. In embodiments in which the mesh support 104 comprises a mesh tube, the conduit 116 may be housed within the mesh tube. This allows the conduit 116 to simply follow the path of the sling 100 when the sling 100 is implanted into the patient so that the conduit 116 extends out of a sling exit site remote from the expansion chamber 112. As explained in more detail below, the conduit 116 may be fluidly connected to an access port placed at a subcutaneous location on the inner thigh to allow for the convenient access to the access port when the patient is in a standing position.

A connector 118 may be provided at the ends 120 of the mesh support 104 for removably attaching the ends 120 of the mesh support 104 to a surgical instrument such as a helical transobturator trocar. The trocar may then be used to implant the sling 100 into the body as known in the art. The conduit 116 may extend from the expansion chamber along the course of the mesh support 104 to the connector 118 so that when mesh support 104 is attached to the connector 118 and passed through the body, the conduit 116 follows the same path through the body and out a desired exit site. In an exemplary method discussed below, a transobturator approach is employed to implant the sling in a tension-free deployment in which the sling 100 extends between the obturator foramina and out exit sites at the inner thigh so that the sling loops under the urethra. The outer portions 108, 110 of the mesh support and the conduit 116 that extend from the exit sites may be trimmed to a desired length and left within the body. The conduit 116 may then be connected to a subcutaneous access port using a fluid connector. As explained in more detail below, an access port may be provided at a desired remote location such as at the inner thigh of the patient to allow for easy access to the port when the patient is in a standing position. This allows for the easy adjustment of the sling with a patient in a standing position by injecting (or removing) expansion fluid into (or from) the expansion chamber 112 through the access port and conduit 116.

The mesh support 104 and mesh envelope 114 may be of a material that promotes tissue ingrowth, such as, by way of example and not limitation, knitted polypropylene mesh, such as GYNEMESH® available from Gynecare. The sling 100 may be of a size commonly used for urethral slings that allows for implantation within a patient's body. For example, a length of about 17 inches and a width of about 1 cm is suitable for a typical female patient, but different sizes could be used depending upon the size of the patient undergoing the procedure. As shown in FIG. 3, the ends 120 of the mesh support 104 may be tapered to ease implantation in the body.

The mesh envelope 114 of the suburethral portion 106 may comprise a double layer of knitted polypropylene mesh having a thickness of about 0.7 mm and openings of about 1 mm. The mesh may be coated with different types of coatings, antibiotics, antibacterials, drugs, etc. A removable sheath (not shown) may be used to cover the sling 100 and keep the sling 100 in a collapsed relatively flat condition when implanting the sling 100 in the body. When the sling 100 is in place, the sheath may be removed to reveal the mesh and allow for tissue ingrowth. An eyelet 122 may be provided on the mesh envelope 114 to allow for easy attachment of the mesh envelope 114 to periurethral tissue using a suture. A minimal lateral dissection may be made in the periurethral tissue to secure the suture to prevent dislocation of the sling 100 and allow the mesh envelope 114 to direct the expansion of the expansion chamber 112.

The expansion chamber 112 is convertible between a collapsed condition and an expanded condition by adding expansion fluid to (or removing expansion fluid from) the expansion chamber 112. This expansion of the expansion chamber 112 provides addition closing pressure to the urethra 102. As shown in FIG. 1, when the sling 100 is implanted in a patient the sling may loop under the urethra 102 so that the suburethral portion 106 is in a slightly curved shape beneath the urethra 102.

Figure 4A:
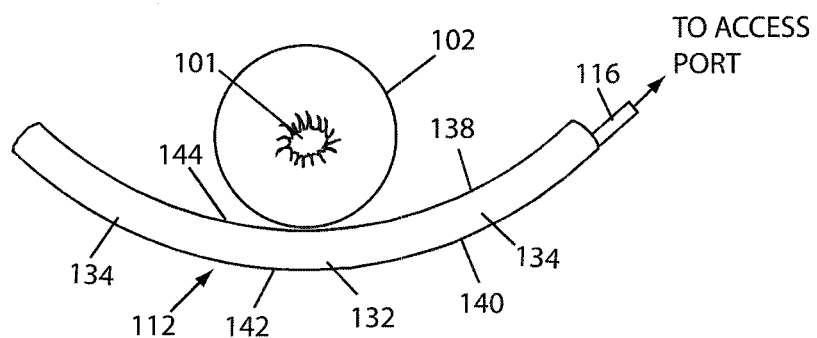
FIGS. 4A-4C show a front view of the expansion portion of an adjustable urethral sling having a single expansion chamber and conduit in accordance with an exemplary embodiment of the invention.

The expansion chamber 112 may be configured to expand into a desired shape. For example, as shown in FIG. 4A, the expansion chamber 112 may comprise a center portion 132 positioned below the urethra 102 to provide an upward closing force to a urethra 102 and outer portions 134 to be positioned to the left and right of the urethra 102 to provide lateral closing pressure to the urethra 102 when expanded. The urethra 102 shown in FIG. 4A has an opening 101 for the passage of urine that does not fully close, thereby leading to incontinence. The center portion 132 may be sized to allow for minimal expansion, whereas the outer portions 134 may be sized to allow for greater expansion. A conduit 116 in fluid communication with the expansion chamber 112 at the center portion 132 may be supplied with fluid from a fluid source as explained in more detail below.

Figure 4B:
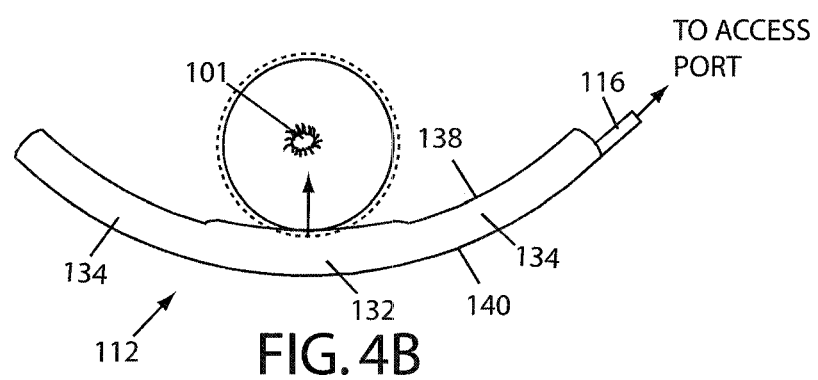
Figure 4C:
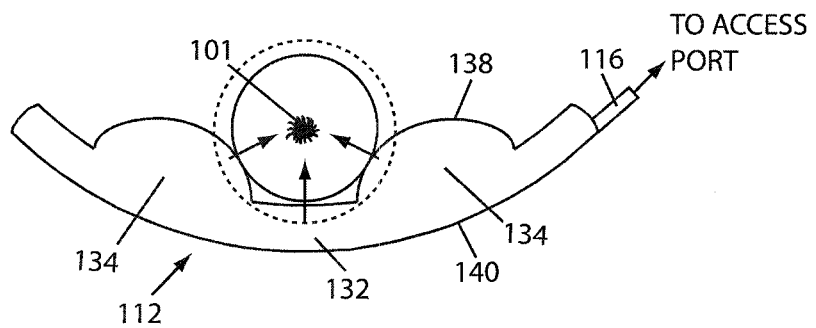

When fluid is added to the expansion chamber 112 via the conduit 116 the fluid will first enter into and expand the center portion 132 (FIG. 4B) to provide an upward force on the urethra 102. This provides additional closing pressure to the urethra 102 to further close the opening 101 in the urethra. Because the center portion 132 is of a limited size, the center portion 132 will not unduly expand and therefore will not raise the urethra 102 to an undesired position. As additional fluid is added to the expansion chamber 112, the fluid will begin to fill the outer portions 134 which will expand to provide lateral forces to the urethra 102 as shown in FIG. 4C. This provides additional closing pressure to the urethra 102 so that the urethra opening 101 is sealed. To prevent obscuring aspects of the invention, the expansion chamber 112 is shown without the mesh envelope 114, but it will be understood by one of skill in the art that the expansion chamber 112 may be housed in the mesh envelope 114 to allow for ingrowth into the mesh and that the expansion of the expansion chamber 112 may occur after tissue ingrowth. As explained in more detail below, the expansion of the expansion chamber 112 may also be controlled by the size and shape of the mesh envelope 114 and the position of the mesh envelope 114 about the urethra 102.

Different portions of the expansion chamber 112 may have different levels of expandability in order to tightly control the expansion of the expansion chamber 112 and the resulting closing forces applied to the urethra 102. For example, a bottom portion 142 of the chamber 112, which when implanted in a female patient will face a vaginal surface, may be constructed of a non-expansion silicone material, such as reinforced Cx material in IPP; whereas, an upper portion 144 of the chamber 112, which may define a suburethral surface of the balloon, may be constructed of a more elastic, expansion silicone material, such as AMS 800 cuff material from American Medical Systems, Inc., Minnetonka, Minn., to allow greater expansion of the upper portion 144. Therefore, when expansion fluid is added to the expansion chamber 112 the upper portion 144 will expand but the lower portion 142 will not so that an upward closing force is applied to the urethra 102.

In some embodiments, the expansion chamber 112 may be arranged to form a U-shaped cradle that provides lateral closing pressure to the urethra 102. The outer portions 134 of the expansion chamber 112 may also have areas of different expandability. For example, to allow expansion inward toward the urethra, an inner wall 138 of the outer portions 134 may be constructed of a material of high expandability and an outer wall 140 constructed of a material of a lesser expandability so that the outer portions 134 expand inward toward the urethra 102 when expansion fluid is added to the expansion chamber 112. In addition, the center bottom portion 132 may be sized so as to allow for minimal expansion. As shown in FIGS. 4B and 4C, when expansion fluid is added to the expansion chamber 112 the bottom center portion 112 expands only a small amount while the outer portions 134 expand upward and inward to form a cradle for providing both bottom and lateral support to the urethra 102. This will better distribute closing forces about the urethra 102 than prior art devices that rely on applying upward forces to the bottom of the urethra. In addition, the sling 100 will not raise the urethra 102 to an undesired position during adjustment or dislocate the sling 102.

Figure 5A:
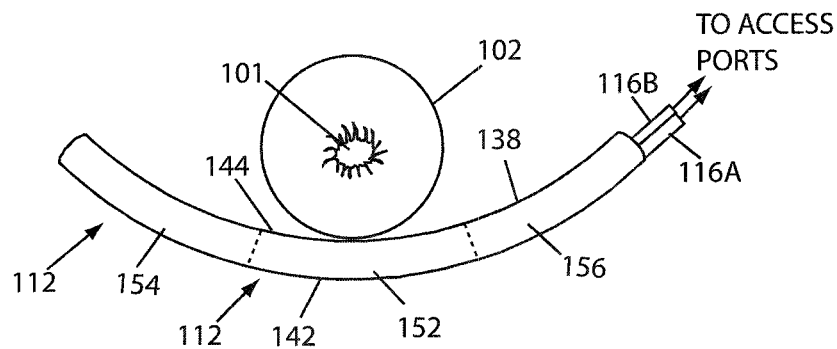
FIGS. 5A-5C show a front view of the expansion portion of an adjustable urethral sling having a plurality of expansion subchambers and a plurality of conduits in accordance with another exemplary embodiment of the invention.
Figure 5B:
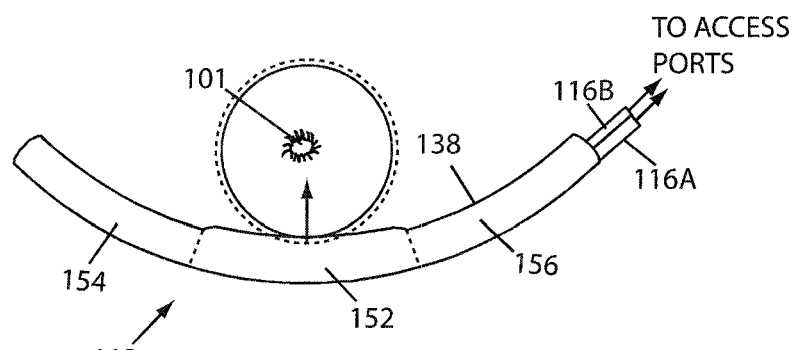
Figure 5C:
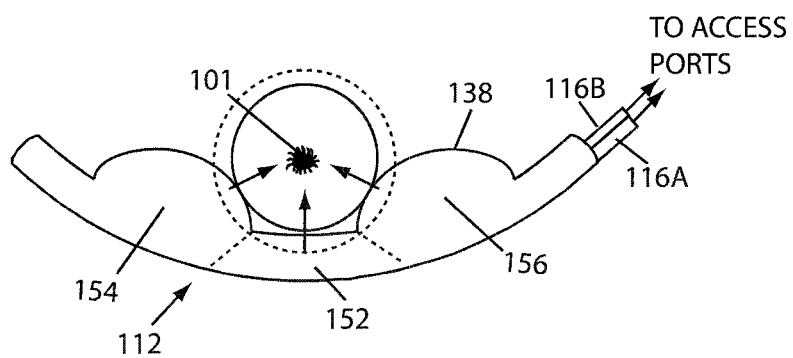

The expansion chamber 112 may also comprise a plurality of expansion subchambers. For example, in the exemplary embodiment shown in FIGS. 5A-5C, the expansion chamber 112 may include center 152, left 154, and right 156 expansion subchambers. The expansion subchambers chambers 152, 154, 156 may be provided within a mesh envelope 114 in an initial generally flat unexpanded condition (FIG. 5A) to provide a small profile to allow for easy insertion and implantation into the body. The subchambers 152, 154, 156 may be constructed to form a desired shape when expanded, such as the U-shaped cradle shown in FIG. 5C, when expanded. In the exemplary embodiment of FIG. 5C the outer subchambers 154, 156 may be expanded two to three times that of the center subchamber 152. This provides lateral closing pressure to the urethra 102 without raising the urethra 102 to an undesired position.

As shown in FIGS. 5A-5C and 6A-6D, multiple conduits 116A-B may be provided to supply expansion fluid to the different subchambers 152, 154, 156. For example, a first conduit 116A may be arranged to supply expansion fluid to the center subchamber 152 and a second conduit 116B arranged to supply expansion fluid to the outer subchambers 154, 156. As shown in FIG. 6A-6C a variety of different shapes may be obtained by injecting different amounts of expansion fluid into the various subchambers 152, 154, 156. This provides a physician with the ability to tightly control the closing pressure that is, applied to the urethra 102 and thereby allows a physician to tailor the urethra closing pressure to the specific needs of the patient.

One advantage of the sling 100 is that the enclosure of the expansion chamber 112 into the mesh envelope 114 allows for tissue ingrowth into the mesh envelope 114 covering the expansion chamber 112. This results in the expansion chamber 112 being enclosed by resilient tissue which allows expansion of the expansion chamber 112 long after implantation in the patient.

Figure 7A:
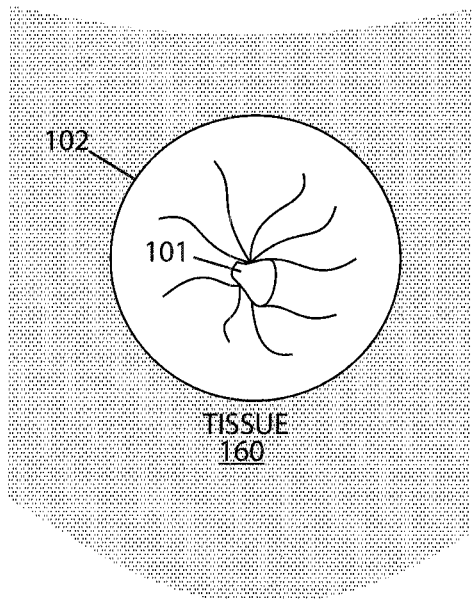
FIGS. 7A-7F show the installation and adjustment of an adjustable urethral sling in accordance with an exemplary embodiment of the invention.
Figure 7B:
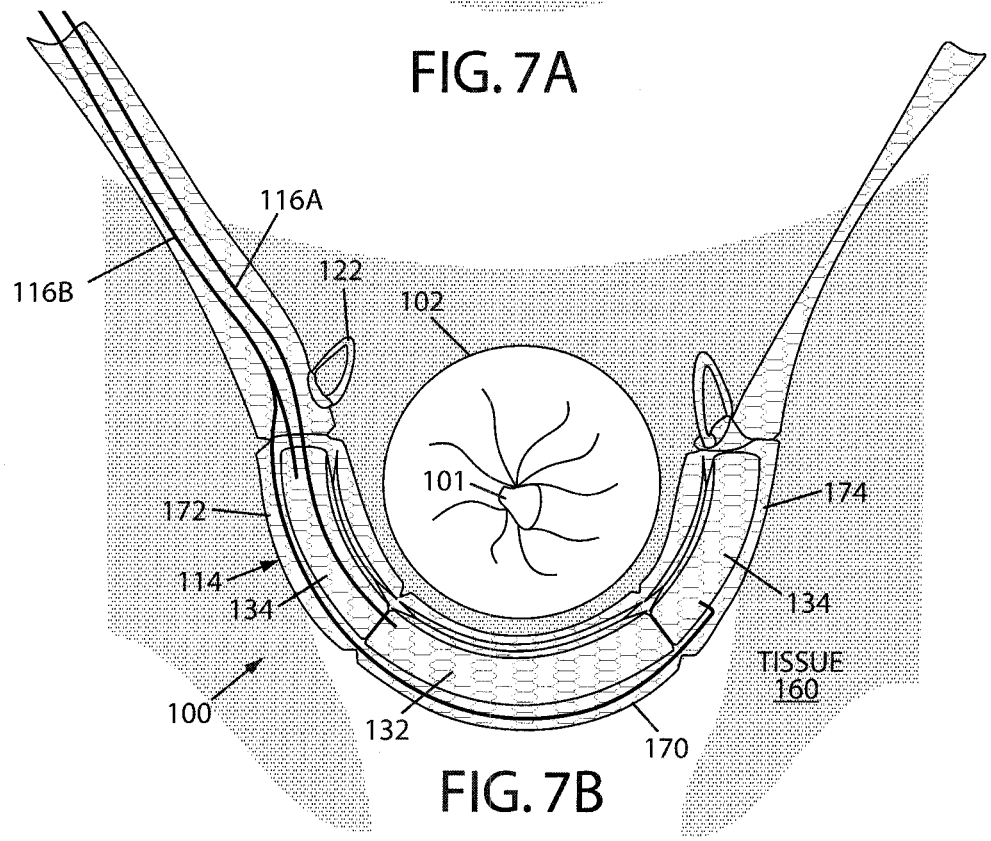
Figure 7C:
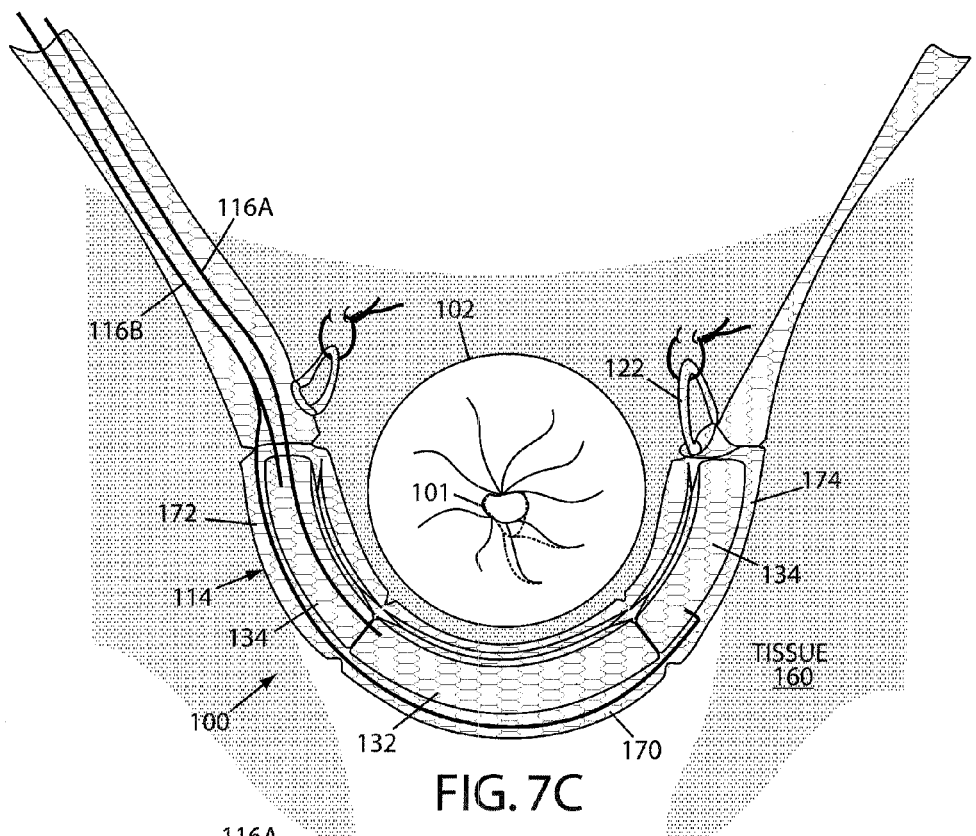

As shown in FIG. 7A a urethra 102 with ISD may not fully close, leaving an opening 101 through which urine may leak. As shown in FIG. 7B, the sling 100 may be implanted below the urethra 102 so that the suburethral portion 106 of the sling 100, the mesh envelope 114, and the expansion chamber 112 are placed beneath the urethra 102. As shown in FIG. 7C, connection means in the form of suture eyelets 122 may be provided for attaching the mesh envelope 114 to periurethral 160 tissue at a desired location. For example, a small lateral incision may be made in the periurethral tissue and a suture passed through the suture eyelet 122 and the periurethral tissue 160. This prevents the sling 100 from being dislocated from its desired midurethral position and provides a structure for tissue ingrowth. The mesh envelope may then extend about the urethra 102 as shown in FIG. 7D where the mesh envelope 114 extends from the left of the urethra 102, under the urethra 102 and up to the right of the urethra 102 and the expansion chamber 112 is in a collapsed condition within the mesh envelope 114.

Figure 7D:
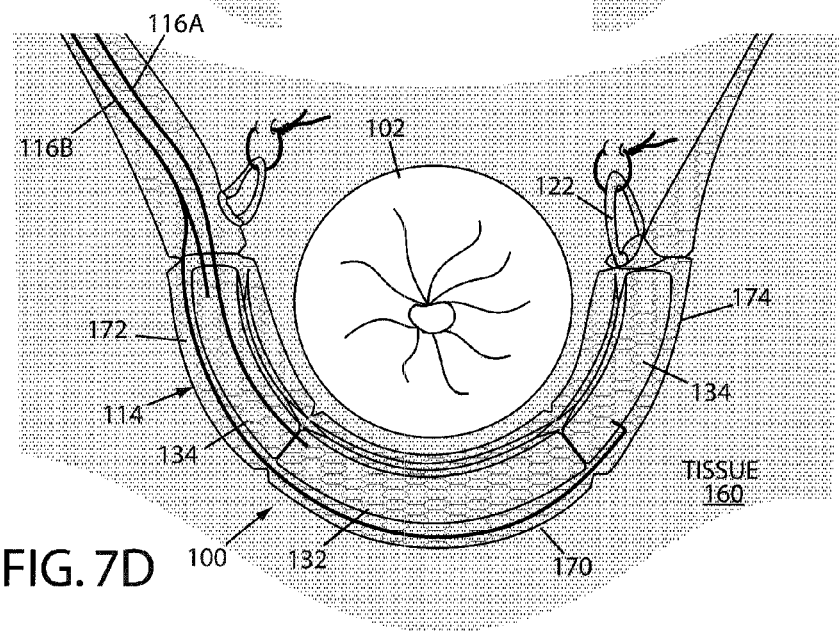
Figure 7E:
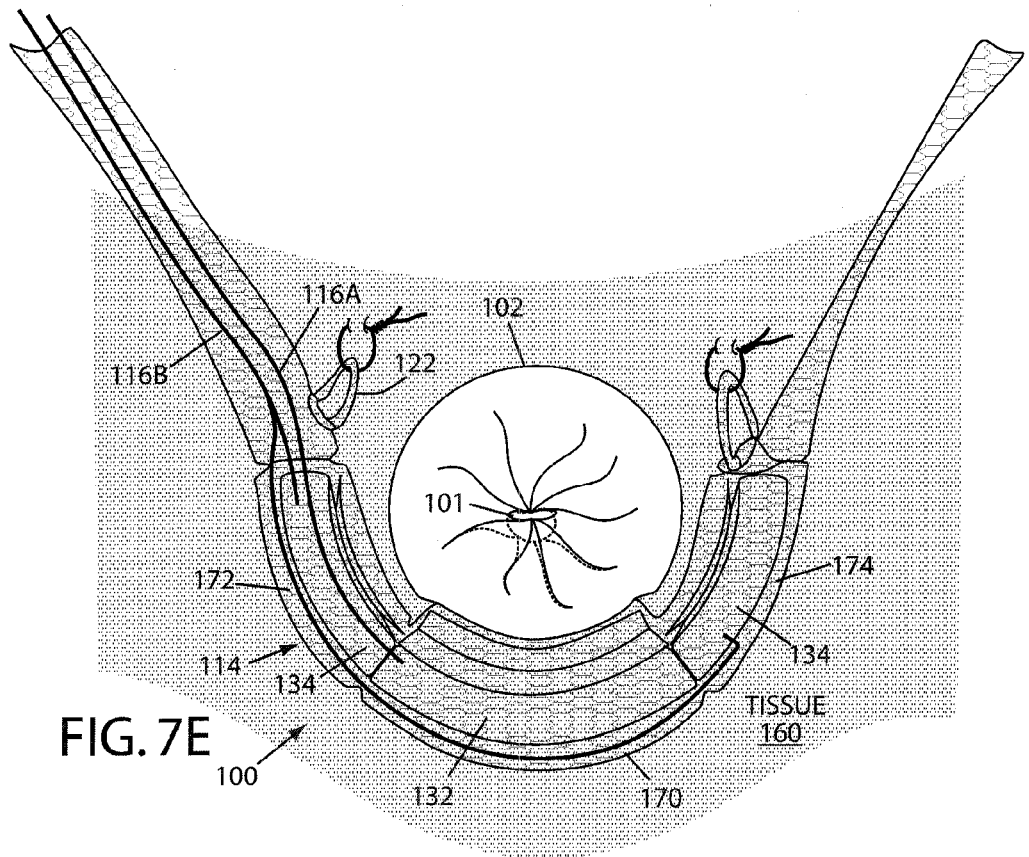
Figure 7F:
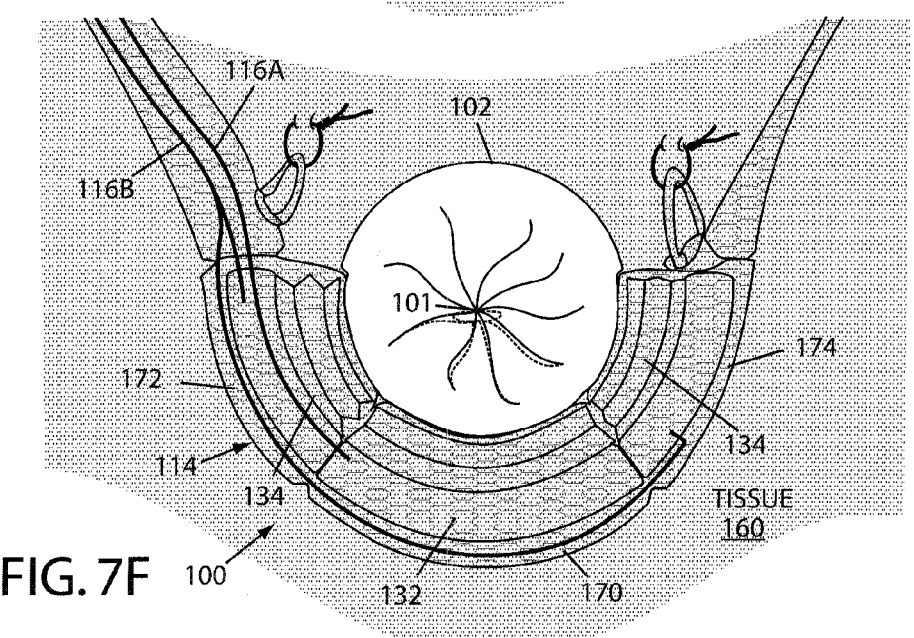

As shown in FIG. 7D normal tissue ingrowth will occur within the mesh envelope 114 to surround the expansion chamber 112. The tissue ingrowth may take around six weeks or so to fully grow. If the patient achieves a desired level of continence after sling implantation, then there is no need to further adjust the sling 100. If the patient does not achieve a desired level of continence after sling implantation, however, then as shown in FIGS. 7E-7F the expansion chamber 112 may be injected with expansion fluid to expand the expansion chamber 112 and apply a desired closing force (shown by arrows) to the urethra 102 to provide a desired continence level. When fluid is added to the expansion chamber 112 the expansion chamber 112 expands within the mesh envelope 114 to form a generally U-shaped cradle that provides upper and lateral closing pressure to the urethra 102. This provides sufficient closing pressure to the urethra 102 without raising the urethra 102 to an undesired height.

The mesh envelope 114 may be shaped to guide or control the expansion of expansion chamber 112. For example, the mesh envelope 114 may have a center portion 170 that corresponds to the center portion 132 of the expansion chamber 112 and outer portions 172, 174 that correspond to outer portions 134 of the expansion chamber. The center 170 and outer 172, 174 portions may be shaped to allow expansion of the center 132 and outer 134 portions therein. For example, the center portion 170 of the mesh envelope 114 may be sized to limit the expansion of the center portion 132 of the expansion chamber to limit the upward movement of the urethra 102 when the expansion chamber 112 is expanded.

As discussed above, to further control the closing pressure applied to the urethra 102 different conduits 116 may be used for expanding different subchambers of an expansion chamber 112 to allow the subchambers to be expanded independently. For example, a first conduit 116A could be in fluid communication with a center expansion subchamber 152 and a second conduit 116B could be in fluid communication with outer subchambers 154, 156. As shown in FIGS. 6A-6D, the subchambers 152, 154, 156 may be supplied with expansion fluid independently to provide different shapes of the expansion chamber 112 and thereby allow a physician to fine tune the closing pressure applied to the urethra 102 for a particular patient by adding or removing expansion fluid from the various subchambers.

The sling 100 may be deployed below the urethra without tension using any suitable method, such as a transobturator approach in which the sling 100 is deployed tension-free between two obturator foramina, as known in the art. For example, an outside-in transobturator approach pioneered by Delorme or an inside-out approach as described by de Leval, both of which are known to one of skill in the art, may be used. To deploy the sling 100, a vaginal incision may be made in the anterior vaginal wall at the level of the middle third of the urethra and the dissection is extended laterally between the anterior vaginal wall and the urethra. A trocar can be attached to a snap connector 118 of the sling 100 and used to deploy the sling as known in the art. The sling 100 may be housed in a removable sheath (not shown) with the sling 100 in a collapsed position to allow for easy passage through the body. The sheath surrounds the sling 100 during positioning as the mesh support 104 of the sling 100 is adherent to tissue. When the sling 100 is properly positioned, the sheath can be removed.

Figure 8:
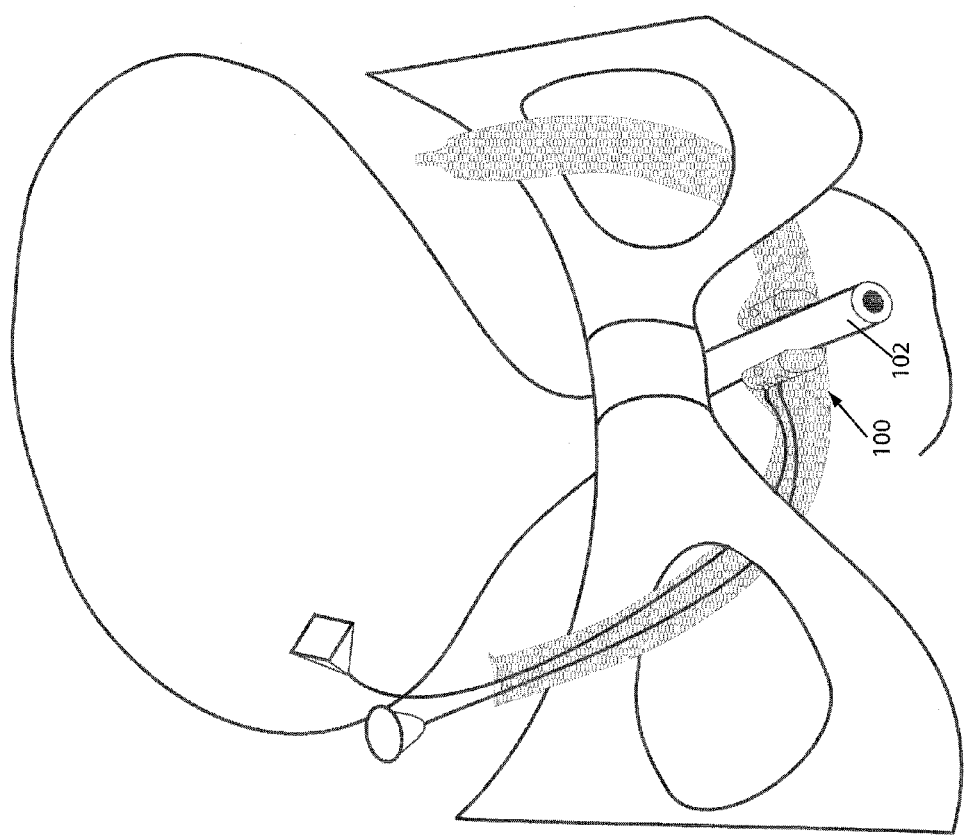
FIG. 8 shows an adjustable urethral sling implanted in a patient in accordance with an exemplary embodiment of the invention.
Figure 9B:
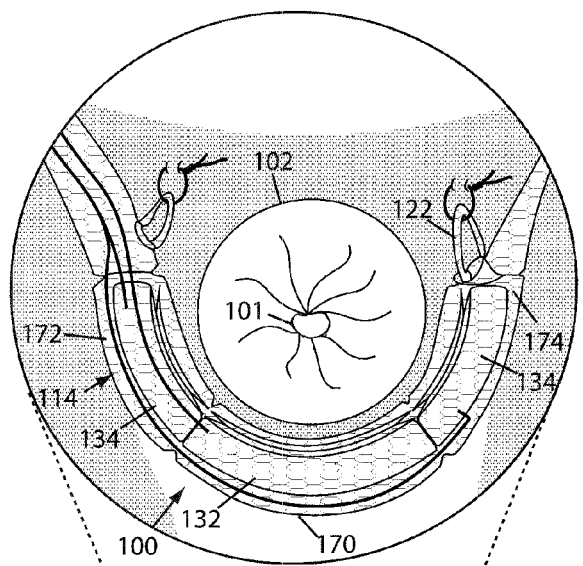
FIG. 9B shows an enlarged portion B-B of FIG. 9A.
Figure 9A:
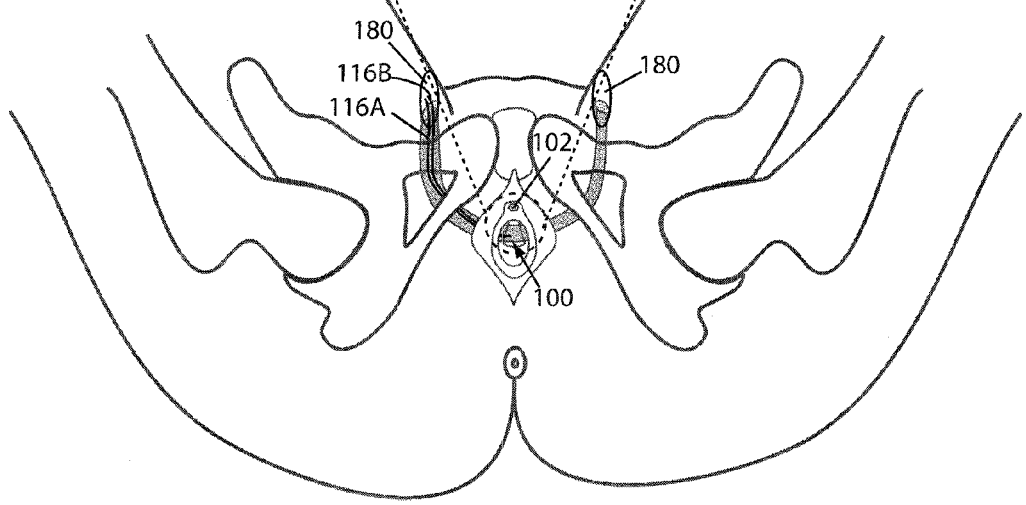
FIG. 9A shows an adjustable sling implanted in a patient in accordance with an exemplary embodiment of the invention.

FIGS. 8 and 9A-B show exemplary embodiments of a deployed sling 100 using a transobturator approach in which the sling 100 is deployed without tension with femoric exit sites 180 at the internal side of the thigh about 2 mm outside and 2 cm in front of the urethral meatus. The suburethral portion 106 of the sling 100 is positioned below the urethra 102. Once the sling 100 is deployed, the sheath (not shown) can be removed and the sling 100 trimmed to a desired length by removing a portion of the mesh support 104 and conduit 116 extending from the exit site 180. As shown in 7C the mesh envelope 114 may be sutured to the periurethral tissue 160 about the urethra 102 using suture eyelets 122. This helps prevent migration of the expansion chamber 112.

As shown in FIGS. 10A-C the conduits 116A-B may then be fluidly coupled to remote access ports 190A-B to provide a means for providing expansion fluid from a location remote from the expansion chamber 112. Metzenbaum scissors may be used to create a small, dependent subcutaneous pouch 184 extending from the exit site 180. In an exemplary embodiment shown in FIG. 10B, the pouch 184 may be may be located 1-2 cm below the exit site 180 and extend to a desired access point. In an exemplary embodiment, the access point may be located at the inner thigh. An access port 190 can be inserted into the pouch 184. In the exemplary embodiment shown in FIG. 10B, the access port 190 includes a housing 192 adapted to receive the needle end of a syringe and port tubing 194 extending from the housing 192 to define a flow path for the two-way flow of an expansion fluid. As shown in FIG. 10B, where multiple conduits 116A-B are employed, multiple access ports 190A-B may be used. The access ports 190A-B may be about 1-1.5 cm in diameter and similar to existing technology for Totally Implantable Venous Access Systems (TIVAS), such as a port-a-cath. In order to assist a physician in determining which injection port is associated with which expansion chamber, the access port housings 192 may have palpably different shapes. For example, as shown in FIG. 10B, one injection port 190A may have a housing 192A with rounded side wall 196 and a second access port 190B may have a housing 192B with squared sidewall 198.

As shown in FIG. 10B, the conduits 116A-B may be coupled to the access ports 190A-B using a connector 200 to fluidly couple the port tubing 194A-B to the conduits 116A-B to thereby provide a flow path between the access ports 190A-B and their associated expansion chambers 152, 154, 156. By way of example and not limitation, the connector 200 may be 90-degree quick connect connector. As discussed above, various conduit and expansion chamber arrangements may be made. For example, a conduit 116 may serve one or more expansion chambers or subchambers. In the exemplary embodiment shown in FIGS. 10A-C, a first conduit 116A may serve a center subchamber 152 and a second conduit 116B may serve lateral expansion chambers 154, 156. As discussed above, the expansion chambers and subchambers may be of different shapes and sizes and have portions with different levels of expandability in order to form a desired shape when expanded and thereby apply a desired closing pressure to the urethra 102. In the exemplary embodiment a U-shaped cradle is formed in which the lateral expansion chambers 154, 156 may be expanded two to three times the expansion of the bottom expansion chamber 152. FIGS. 11A-11C show exemplary embodiments of different expanded shapes that may be obtained by providing different amounts of fluid to the various subchambers 152, 154, 156 of an expansion chamber 112. The location of the access ports 190A-B at the inner thigh makes them easily accessible for a physician and innocuous for a patient.

This arrangement will allow postoperative incontinence adjustment at any time without anesthesia. It may be desirable to allow sufficient time for ingrowth into the mesh envelope 114, such as about six weeks after surgery, before adjusting the apparatus 100. The access port 190 is easily accessible in a physician's office using a syringe to inject expansion fluid into the expansion chamber 112 (or to remove expansion fluid from the chamber) using a syringe. In an exemplary embodiment, a 1 cc insulin or tuberculin syringe with 28 gauge needle or small diameter blunt needle may be used to access the access port 190. The patient's bladder may be filled via a catheter with normal saline, and saline injected until cough or Valsalva yields no further leakage. Expansion fluid could be added gradually to the expansion chamber 112 with the patient in a standing position, which is the position most associated with SUI in women. Continued challenges can be made, such as cough, Valsalva, bending or jumping, and the amount of expansion fluid within the expansion chamber 112 adjusted to achieve a desired level of continence. Various expansion fluids can be used, such as by way of example and not limitation, saline, H2O or IV contrast.

Implantation of the sling 100 may be performed as an outpatient procedure and postop Foley catheter drainage will most likely not be required. The procedure will not take appreciably longer than a standard transobturator sling and there is no additional risk or recovery time. For the 15-20% of patients who do not achieve their desired level of continence with placement of a tension free mid-urethral sling, this would provide a simple, desirable alternative to secondary periurethral expansion fluids or conversion to retropubic mid urethral or formal pubovaginal slings. Because of the ingrowth tissue in the mesh envelope about the expansion chamber the sling can be adjusted for long periods of time after implantation. Although the exemplary embodiments were discussed in the context of the treatment of male SUI, the apparatus is well suited to treat male SUI from causes not limited to post-prostatectomy incontinence. With the periurethral fixation, and the elongated U-shaped expandable expansion chamber to provide both compressive forces to 75% of the urethra and relocation of the urethra into its natural retropubic location, most male incontinence will be successfully treated.

In light of the foregoing disclosure of the invention and description of certain preferred embodiments, those who are skilled in this area of technology will readily understand that various modifications and adaptations can be made without departing from the true scope and spirit of the invention. All such modifications and adaptations are intended to be covered by the following claims. Thus, the foregoing has broadly outlined some of the more pertinent aspects and features of the present invention. These should be construed to be merely illustrative of some of the more prominent features and applications of the invention. Other beneficial results can be obtained by applying the disclosed information in a different manner or by modifying the disclosed embodiments. Accordingly, other aspects and a more comprehensive understanding of the invention may be obtained by referring to the detailed description of the exemplary embodiments taken in conjunction with the accompanying drawings, in addition to the scope of the invention defined by the claims.

What is claimed is:

1. A urethral sling system, comprising:
a flexible mesh support adapted for implantation into a body;
a collapsible mesh envelope located at a suburethral portion of the flexible mesh support;
an expansion chamber housed within the collapsible mesh envelope;
a first conduit in fluid communication with the expansion chamber;
a first access port fluidly coupled to the first conduit;
a second access port; and
a second conduit fluidly coupled to the expansion chamber and the second access port.

2. The urethral sling system of claim 1, wherein said mesh envelope comprises a two layer mesh.

3. The urethral sling system of claim 1, wherein said flexible mesh support comprises a mesh tube.

4. The urethral sling system of claim 1, wherein the first conduit is in fluid communication with the expansion chamber, the first conduit extending from the expansion chamber and following the flexible mesh support.

5. The urethral sling system of claim 4, wherein said first conduit is attached to said flexible mesh support.

6. The urethral sling system of claim 1, wherein said expansion chamber comprises a plurality of expansion subchambers.

7. The urethral sling system of claim 1, wherein said expansion chamber is configured to form a U-shaped cradle when expanded.

8. The urethral sling system of claim 1, further comprising: attachments means for attaching said mesh envelope to periurethral tissue.

9. The urethral sling system of claim 1 wherein said collapsible mesh envelope is shaped to receive the expansion chamber in an expanded condition.

10. The urethral sling system of claim 1, wherein:
said expansion chamber comprises a plurality of expansion subchambers; and
wherein the first conduit is in fluid communication with a first expansion subchamber and the second conduit is in fluid communication with a second expansion subchamber.

11. The urethral sling system of claim 1, wherein the first access port is provided at a remote location from the expansion chamber.

12. The urethral sling system of claim 1, wherein the first access port is positioned subcutaneously at a remote location from the expansion chamber.

13. The urethral sling system of claim 1, wherein said first access port and said second access port have palpably different housings.

14. The urethral sling system of claim 1, wherein said expansion chamber comprises:
a center portion to provide support under the urethra;
a left outer portion to provide lateral support to the urethra when expanded; and
a right outer portion to provide lateral support when expanded.

15. A urethral sling system, comprising:
a flexible mesh support adapted for implantation into a body;
a collapsible mesh envelope located at a suburethral portion of the flexible mesh support;
an expansion chamber housed within the collapsible mesh envelope;
a first conduit in fluid communication with the expansion chamber; and
an access port fluidly coupled to the conduit,
wherein said expansion chamber, comprises:
a center portion to provide support under the urethra;
a left outer portion to provide lateral support to the urethra when expanded; and
a right outer portion to provide lateral support when expanded, wherein the first conduit is in fluid communication with said center portion and a second conduit is in fluid communication with said left and right outer portions.

16. A method, comprising:
implanting a urethral sling within a patient, the urethral sling looping under the urethra so that an expansion chamber enclosed within a collapsible mesh envelope is positioned under the urethra, the expansion chamber in an initial collapsed condition, the urethral sling comprising, a flexible mesh support adapted for implantation into a body;
the collapsible mesh envelope located at a suburethral portion of the flexible mesh support;
the expansion chamber housed within the collapsible mesh envelope;
a conduit in fluid communication with the expansion chamber; and
an access port fluidly coupled to the conduit;
a second access port; and
a second conduit fluidly coupled to the expansion chamber and the second access port.

17. The method of claim 16, further comprising:
wherein the conduit extends along the flexible mesh support and out an exit site and trimming the flexible mesh support and the conduit to a desired size.

18. The method of claim 16, further comprising:
attaching the mesh envelope to periurethral tissue.

19. The method of claim 16, further comprising:
making a subcutaneous pouch at a remote location from the expansion chamber.

20. The method of claim 16, further comprising:
inserting the access port in a subcutaneous pocket remote from the expansion chamber.

21. The method of claim 20, further comprising:
fluidly coupling the access port to the conduit to form a flow path for expansion fluid between the access port and the expansion chamber.

22. The method of claim 21, further comprising:
injecting an expansion fluid into the access port to expand the expansion chamber.

23. The method of claim 22, further comprising injecting an expansion fluid into the access port to expand the expansion chamber and mesh envelope after tissue ingrowth in the mesh envelope.

\* \* \* \* \*